United States Patent [19]

Slaugh

[11] 4,335,022

[45] Jun. 15, 1982

[54] MODIFIED SILICA COMPOSITION

[75] Inventor: Lynn H. Slaugh, Houston, Tex.

[73] Assignee: Shell Oil Company, Houston, Tex.

[21] Appl. No.: 219,279

[22] Filed: Dec. 22, 1980

Related U.S. Application Data

[63] Continuation-in-part of Ser. No. 61,205, Jul. 27, 1979, abandoned.

[51] Int. Cl.³ .............................................. B01J 21/12
[52] U.S. Cl. ................................................ 252/455 R
[58] Field of Search .................... 252/455 R; 423/628, 423/645

[56] References Cited

U.S. PATENT DOCUMENTS

| | | | |
|---|---|---|---|
| 3,146,209 | 8/1964 | Byrne et al. | 252/455 R |
| 3,305,590 | 2/1967 | Pollitzer et al. | 252/455 R |
| 3,415,759 | 12/1968 | Johnson | 252/455 R |
| 3,437,605 | 4/1969 | Keith | 252/477 R |
| 3,501,333 | 3/1970 | Groves et al. | 117/47 |
| 3,823,226 | 7/1974 | Brower et al. | 423/645 |
| 3,844,853 | 10/1974 | Matzek | 423/645 |

*Primary Examiner*—Carl F. Dees

[57] ABSTRACT

A novel siliceous composition prepared by impregnating porous silica with aluminum hydride and subsequently heating the impregnated silica to a temperature of from about 300° C. to about 900° C. in a non-oxidizing environment. The composition is useful as a catalyst in reactions catalyzed by acid catalysts.

12 Claims, No Drawings

MODIFIED SILICA COMPOSITION

This application is a continuation-in-part of application Ser. No. 061,205, filed July 27, 1979 and now abandoned.

BACKGROUND OF THE INVENTION

1. Field of the Invention

This invention relates to novel siliceous compositions prepared by reacting porous silica with aluminum hydride. These compositions are useful as catalysts, particularly as catalysts for acid catalyzed reactions.

2. Background of the Invention

Aluminum hydride has been decomposed to produce aluminum metal coatings on glass objects in U.S. Pat. No. 3,501,333, issued Mar. 17, 1970. These processes are typically low temperature processes, below 250° C. The instant compositions contain no aluminum metal.

U.S. Pat. No. 3,146,209, issued Aug. 25, 1964, teaches a method for producing an aluminum hydride containing silica in which bound water molecules on the silica surface are replaced with aluminum hydride molecules to provide a solid composition basically comprising silica and a hydride source attached thereto. There is no teaching in this reference of any subsequent treatment being applied to their gel material to produce an oxide material comparable to the instant compositions.

U.S. Pat. No. 3,305,590, issued Feb. 21, 1967, discloses a general process for making alumino-silicates. This reference generally teaches impregnation of silica with any decomposable aluminum salt. The aluminum hydride used to prepare the instant composition is not considered a salt but rather is a covalent compound (see Metal Hydrides, Mueller et al, p. 545, Academic Press, 1968).

The compositions of the instant invention have significantly altered catalytic properties over conventional silica supports. Significant improvement in catalyst life is noted. The instant compositions are useful for catalyzing acid catalyzed reaction.

SUMMARY OF THE INVENTION

Unique siliceous materials are prepared by impregnating porous silica with solutions of aluminum hydride and subsequently heating the impregnated silica in a non-oxidizing environment to temperatures of from about 300° to 900° C. These materials have highly acid sites and are useful as catalysts and catalyst supports for acid catalyzed reactions.

DESCRIPTION OF THE PREFERRED EMBODIMENTS

The porous silicas used in the preparation of the instant composition are readily available commercially and are known as silica gels which are essentially substantially dehydrated amorphorous silica. These materials are available in various density grades, from low density with surface areas ranging from about 100–200 $m^2/g$, to regular density with surface areas up to about 800 $m^2/g$. These commercially available materials are used as desiccants, selective adsorbents, catalysts and catalyst supports. The porous silica may contain minor proportions of other materials without departing from the scope of the invention such as for example alumina and carbon. Prior to use the porous silica should be substantially free of adsorbed water, i.e. "substantially dehydrated". The residuum of chemically bound water, i.e. water of hydration, is not harmful to the process of this invention. The adsorbed or free water is removed by heating the porous silica at temperatures from about 200° to about 900° C. prior to contact with the aluminum hydride impregnating solution. Any environment that will provide for drying is suitable, such as air, vacuum, inert gas such as nitrogen, etc. The dried porous silica should be kept away from a humid atmosphere after drying. A convenient drying atmosphere is that used to heat the impregnated silica, such as nitrogen.

The aluminum hydride suitable for use in this invention is prepared commercially by reacting at room temperature lithium aluminum hydride and aluminum chloride in diethyl ether ($Et_2O$). The product is isolated in high yield by decanting and drying at room temperature. The product is analyzed as $AlH_3 \cdot \frac{1}{3} Et_2O$. For purposes of this invention the aluminum hydride is dissolved in a suitable organic solvent. The prime requirement on the solvent is that it be anhydrous and non-hydroxyl containing since water and alcohol react with aluminum hydride. Suitable solvents are for example, ethers, such as diethyl ether, tetrahydrofuran, pyridine, benzene, toluene, chloroform and the like.

To prepare the compositions of the instant invention, porous silica suitably dried of adsorbed water is contacted with a solution of aluminum hydride in appropriate proportions as to provide the desired amount of aluminum hydride per unit weight of silica. A suitable method of impregnation is described in U.S. Pat. No. 3,146,209, issued Aug. 25, 1964. The impregnated silica is dried of solvent and then heated (activated) in a non-oxidizing atmosphere at temperatures from about 300° C. to about 900° C., more preferably at temperatures of from about 450° C. to about 750° C. The drying step is preferably carried out in the initial stages of the heating step. Suitable non-oxidizing atmospheres are inert atmospheres such as nitrogen, helium, argon, vacuum, etc; and reducing atmospheres such as hydrogen, carbon monoxide, etc. Drying temperatures are not critical and depend on the particular solvent and will range from about 60 to about 100% of the boiling point (absolute). Drying and heating times are not critical and depend upon temperatures. They are readily determined by simple experimentation. Five minutes to one hour are usually sufficient. Typically the amount of aluminum hydride (measured as aluminum metal) added will range from about 0.01 to about 35, preferably from about 0.1 to about 25 and more preferably from about 1 to about 10 percent by weight of the total composition. Different reactions will require different optimum amounts of aluminum hydride added. For example, for dehydrocoupling of isobutenes to aromatics the aluminum hydride added will range from about 2 to about 10 percent by weight of aluminum per total weight of composition.

The compositions of the invention find use for catalyzing acid catalyzed reactions. The compositions of this invention are acidic as compared to the essentially neutral silicas. The composition of the invention are similar in acidity to the acidic binary alumina-silica gels. While the exact physical structure of the instant composition is not known, it is speculated that the decomposition of the aluminum hydride on the silica surface produces localized Lewis acid sites having an atomic ratio of oxygen to metal ratios lower than the normal oxygen to silica ratio. Analysis of the instant composition indicated no aluminum metal had been deposited on the surface and an insignificant amount of residual aluminum hydride remained. These findings are consistent with the above theory of aluminum hydride reacting with the silica.

The compounds of the instant invention prepared using the covalent aluminum hydride compounds differ significantly in their physical characteristic when compared to compounds prepared using decomposable salts. For example, materials prepared using aluminum hydride were compared to those prepared using aluminum nitrate by using X-Ray Photoelectric Spectroscopy (XPS or ESCA). This analysis allowed the relative number of silicon, aluminum and oxygen atoms on the surface to be determined. The composition originating from the $AlH_3$ treatment exhibited a very high ratio of Al/Si atoms on the surface compared to a composition prepared via $Al(NO_3)_3$ wet impregnation. These data suggest concentration of the Al atoms on the external surface when $AlH_3$ is the reactant but not when $Al(NO_3)_3$ is the impregnating material. This concept was confirmed by re-analysis of the compositions after they were ground to expose their interiors. The ratio of Al/Si was substantially less after grinding in the $AlH_3$/$SiO_3$ case but about the same or a little higher in the $Al(NO_3)_3$/$Al_2O_3$ case. The results are summarized below in Table I.

| Relative Number of Atoms Detected on Surface by XPS (ESCA) | | | | |
|---|---|---|---|---|
| | $AlH_3/SiO_2$[b] | | $Al(NO_3)_3/SiO_2$[b] | |
| Sample Treatment | 20–30 Mesh Particles | Ground[a] to Powder | 20–30 Mesh Particles | Ground[a] to Powder |
| Si[c] | 100 | 100 | 100 | 100 |
| Al | 25 | 9.9 | 5.0 | 6.5 |
| O | 184 | 164 | 168 | 164 |

[a]Ground to a fine powder in Argon.
[b]Impregnated materials were activated in a stream of $N_2$ in 50° stages to 700° C.. The aluminum content of the final product was about 3.8–4% wt. Davison 57 grade $SiO_2$ was employed as the support.
[c]Data normalized to Si = 100.

The preparation of the compositions of the instant invention and their utilization as catalysts will be further described below by the following illustrative embodiments which are provided for illustration and are not to be construed as limiting the invention.

Illustrative Embodiments

Composition Preparation

A porous silica gel (Davison Grade 57, surface area of 300 m²/g, pore volume of 1.0 cc/gm and density of 0.4 gm/cc) 20–30 mesh was pretreated in dry nitrogen at 700° C. for one half an hour. Exposure of the dried support to air was avoided. In a glove box with a dry nitrogen atmosphere 5 grams of the dried support was impregnated with a solution prepared by dissolving 0.4 grams of $AlH_3.1/3(Et_2O)$ in 8 ml of tetrahydrofuran. The impregnated material was placed in a vycor tube and dry nitrogen passed over the catalyst as the temperature was increased in 50° C. intervals (15 min. at each temp.) to 700° C. and held at this temperature for 15 minutes. The finished composition was cooled with a nitrogen flow of 40 ml/min.

Similar compositions were prepared using high surface area silica gels (e.g. Davison Grade 03, surface area of 750 m²/g, pore volume of 0.43 gm/cc and density of 0.7 g/cc).

Similar compositions were made by activating at 500° to 550° C.

Utilization as Catalysts

Illustrative but not all inclusive examples of the use of the instant composition as catalysts are provided below.

Isobutene Dehydrocoupling

Compositions according to this invention were prepared as described above and were tested for catalytic activity for the dehydrocoupling of isobutene to aromatics. Example 1 shows that untreated silica gel has no activity but the same silica with 3% added $AlH_3$ (example 2) shows a 20% selectivity to aromatics. A conventional 75% $SiO_2$/25%$Al_2O_3$ (Example 3) also shows selectivity to aromatics but somewhat less than that of the instant invention. For this particular reaction the instant compositions are superior to neat silica and somewhat better than the silica-aluminas.

In general, the isobutene dehydrocoupling reaction is carried at a temperature of from about 450° C. to about 650° C.

TABLE II

Conversion of Isobutene
Reaction Temperature - 500° C.
GHSV - 600

| Example | Catalyst[b] | Conv. of i-$C_4H_8$ % | Selectivity, Mole % (based on $C_4$ equivalents)[c] | | | |
|---|---|---|---|---|---|---|
| | | | $CH_4$ | $C_2$'s | $C_3$'s | I—$C_4H_{16}$ |
| I-1 | $SiO_2$[a] | 0 | — | — | — | — |
| I-2 | $AlH_3/SiO_2$[a] 3.0% wt added Al | 84 | 3.9 | 6.0 | 16.1 | 33.8 |
| I-3 | 75% $SiO_2$/ 25% $Al_3O_3$[d] | 87 | 1.9 | 2.7 | 22.4 | 27.3 |

| Example | n-$C_4H_{10}$ | n-$C_4H_8$ | Selectivity, Mole % (based on $C_4$ equivalents)[c] | | |
|---|---|---|---|---|---|
| | | | benzene + toluene | xylenes | total aromatics |
| I-1 | — | — | — | — | — |
| I-2 | 2.0 | 23.6 | 3.8 | 9.0 | 20.6 |
| I-3 | 3.8 | 26.3 | 1.4 | 4.6 | 13.2 |

[a]Davison grade 57 $SiO_2$, surface area of 300 m²/gm, pore volume of 1.0 cc/gm and density of 0.4 gm/cc
[b]All materials were activated by heating in a stream of nitrogen at 550° C.
[c]The $C_2$'s and $C_3$'s were mainly olefins
[d]Davison Grade 980-25, 75% $SiO_2$/25% $Al_2O_3$, surface area of 325 m²/g, pore volume of 0.45 gm/cc and density of 0.73 gm/cc.

Alkylation of Benzene with Alkenes

A catalyst according to the invention prepared as described above (3.8% of Al added, activated at 700° C.) was compared to a catalyst prepared by impregnating Davison Grade 57 silica gel with aluminum nitrate (activated at 700° C.) and further compared with a commercial 75% $SiO_2$/25% $Al_2O_3$ gel (Davison 980-25), for the alkylation of benzene with propylene. Feed was benzene, propane and propylene in 15:2:1 weight ratio. Pressure was 400 psig. The temperature was adjusted to give an initial conversion of about 10% on benzene. Both the aluminum hydride impregnated aluminum and the aluminum nitrate impregnated aluminum were much more active than the 25 $Al_2O_3$-75$SiO_2$, the latter material requiring a temperature of 200° C. to achieve 12% conversion whereas the former two materials only require a temperature of 140° C. to achieve 10% conversion. Catalyst lifetimes (conversion dropoff to about 60%) of the different materials were considerably different. The 25 $Al_2O_3$-75$SiO_2$ had a life time of about 30–40 hours. The aluminum nitrate impregnated aluminum had a lifetime of about 40–50 hours, but the aluminum hydride impregnated alumina had a life time of about 160–180 hours. The aluminum hydride impregnated alumina could be regenerated to initial activity by heating first in air to about 450° C. and then in nitrogen to about 700° C.

Similar results were obtained using 1-dodecene. In general, for the alkylation of benzene with alkenes, a temperature of about $-20°$ C. to about 350° C., preferably from about 0°–250° C. is utilized.

Transalkylation of Benzene and Diisopropylbenzene

A catalyst according to this invention prepared as described above (3.8% wt. added aluminum; Davison Grade 57, 20–30 mesh silica gel; activated in nitrogen at 700°) was used to transalkylate benzene and diisopropyl benzene to cumene. Ten milliliters of catalyst was used in a vycor tube. The feed was benzene and diisopropyl benzene in a 5:1 molar ratio, pressure was 400 psig and temperature was 280° C. The LHSV was about 2. After 2 hours a sample was taken and analyzed as follows: $C_3$-1.8% wt; benzene-78.5% wt; diisopropyl benzene-12.4% wt; cumene-6.5% wt; and triisopropyl benzene-0.83% wt.

In general for the transalkylation of benzene and dialkylbenzene to alkylbenzene a temperature from about 175°–450° C., preferably about 200°–300° C. is utilized.

Oligomerization of Isobutene

A catalyst according to this invention prepared as described above (3.8% wt added aluminum; Davison Grade 57 20–30 mesh activated at 550° C.) was tested for oligomerization activity. Fourteen milliliters of catalyst was used in a vycor tube. Isobutene was fed at a GHSV of 600, at atmospheric pressure. The results are shown in the table below. As can be seen, lower temperatures promote the oligomerization to higher carbon numbers. Regenerated catalyst behaved similarly to fresh catalysts.

In general for oligomerizing alkene, a temperature from about 0°–300° C., preferably from about 50°–200° C. is utilized.

TABLE III

| | OLIGOMERIZATION OF ISOBUTENE | | | | |
|---|---|---|---|---|---|
| Example | Catalyst | Reaction Temp. °C. | Conv. of i-$C_4H_8$ % | Selectivity, Mole % (Based on $C_4$ equivalents) | |
| | | | | $C_8=$ $C_{12}=$ $C_{16}=$ | |
| II-1 | AlH$_3$/Davison SiO$_2$ Grade 57 3.8% Al | 150 | 77.0 | 57  43  — | |
| II-2 | AlH$_3$/Davison SiO$_2$ Grade 57 3.8% Al | 65 | 98.0 | 3  81  16 | |

Isomerization of m-xylene

A catalyst according to this invention prepared as described above (3.8% wt. added aluminum; Davison Grade 57, 20–30 mesh; activated at 550° C.) was tested for isomerization activity. Fourteen milliliters of catalyst was used in a vycor reactor tube. m-Xylene was pumped in at 50 ml/hour (LHSV=3.6) and the reaction was run for one-half hour at 250° C., 300° C., 400° C., 450° C. and 500° C. Very little conversion was noted up to 400° C. At 450° C. analysis of the product showed: 13.6% wt p-xylene; 76.7% wt m-xylene; and 9.6% wt o-xylene. At 500° C. product analysis shows: 15.2% wt p-xylene; 70.9% wt m-xylene; 13.9% wt o-xylene with a trace of toluene.

In general for isomerizing dialkylbenzenes, particularly diethylbenzenes, a temperature range of from 350°–600° C., preferably about 400°–550° C. is utilized.

Conversion of Alcohols to Ethers

A catalyst according to this invention prepared as described above (3.8% wt. added aluminum; Davison Grade 57, 20–30 mesh; activated at 700° C.) was tested for activity in converting alcohols to ethers. Fourteen milliliters of catalyst was used in a vycor tube reactor.

1,4-Butanediol was pumped through the reactor at a LHSV of 2 cocurrent with a nitrogen flow of 40 ml/minute at atmospheric pressure. At 200° C. conversion of the alcohol to tetrahydrofuran was found to be 13.7% wt. When the LHSV was lowered to 1, the conversion to tetrahydrofuran increased to 35.1% wt. At 250° C. the conversion to tetrahydrofuran was substantially 100%.

Methanol was pumped through the reactor at a flow of 1 LHSV cocurrent with a nitrogen flow of 40 ml/minute. Product analysis showed that at 250° C., 300° C., and 350° C. conversion of methanol to dimethyl ether was 7, 33 and 65 percent by weight respectively.

It can be seen from above that different alcohols have different reaction temperatures. For methanol, a desirable reaction temperature is from about 200°–550° C., preferably from about 250°–450° C. and for 1,4-butanediol from about 150°–500° C., preferably from about 150°–300° C.

Conversion of Phenol to Aniline

A catalyst according to this invention prepared as described above (4% wt added aluminum; Davison Grade 57, 20–30 mesh; activated at 700° C.) was tested for its activity in converting phenol to aniline. The feed was NH$_3$: phenol at a mole ratio of 17.6:1. The results are shown below in Table IV. Reaction temperature for converting aromatic alcohols to the corresponding amines range from about 250°–550° C., preferably from about 300°–450° C. and pressures range from about atmospheric to 5000 psig, preferably from about 500°–4000 psig.

TABLE IV

| | Conversion of Phenol to Aniline | | | | | | |
|---|---|---|---|---|---|---|---|
| Example | Volume of Catalyst, cc | Feed Rate, cc/hr | Reaction Temp., °C. | Reaction Press., psig | Conv. of Phenol, w % | Selectivity, wt % | |
| | | | | | | Aniline | Diphenyl Amine |
| III-1 | 18 | 10 | 225 | 3600 | 0 | 0 | 0 |
| III-2 | 18 | 10 | 300 | 3600 | 6 | 100 | 0 |
| III-3 | 17 | 10 | 350 | 3600 | 26 | 99.7 | 0.3 |
| III-4 | 17 | 10 | 380 | 3600 | 44 | 98 | 2 |
| III-5 | 19 | 5 | 400 | 2500 | 63 | 90 | 10 |
| III-6 | 19 | 5 | 425 | 1500 | 85 | 89 | 11 |

What is claimed is:

1. A process for preparing a siliceous composition which comprises impregnating a substantially dehydrated amorphorous silica gel with aluminum hydride dissolved in an anhydrous, non-hydroxyl containing organic solvent, drying the impregnated silica to remove the solvent and subsequently heating the impregnated silica at a temperature of about 300° to about 900° C. in a non-oxidizing atmosphere.

2. The process of claim 1 wherein the impregnated silica is subsequently heated to a temperature of about 450° C. to about 750° C.

3. The process of claim 1 wherein the impregnated silica before heating contains from about 0.01 to about 35 percent by weight of aluminum hydride measured as aluminum metal.

4. The process of claim 1 wherein the impregnated silica before heating contains from about 0.1 to about 25 percent by weight of aluminum hydride measured as the metal.

5. The process of claim 1 wherein the impregnated silica before heating contains from about 1 to about 10 percent by weight of aluminum hydride measured as the metal.

6. The process of claim 5 wherein the aluminum hydride is $AlH_3 \cdot \frac{1}{3}(CH_3CH_2)_2O$ dissolved in tetrahydrofuran or diethyl ether.

7. The process of claim 2 wherein the impregnated silica before heating contains from about 0.01 to about 35 percent by weight of aluminum hydride measured as the metal.

8. The process of claim 2 wherein the impregnated silica before heating contains from about 0.1 to about 25 percent by weight of aluminum hydride measured as the metal.

9. The process of claim 2 wherein the impregnated silica before heating contains from about 1 to about 10 percent by weight of aluminum hydride measured as the metal.

10. The process of claim 9 wherein the aluminum hydride is $AlH_3 \cdot 1/3(CH_3CH_2)_2O$ dissolved in tetrahydrofuran or diethyl ether.

11. A composition as prepared by the process of claim 1.

12. A composition as prepared by the process of claims 2, 3, 4, 5, 6, 7, 8, 9 or 10.

* * * * *